US00PP29754P2

(12) United States Plant Patent
Klemm et al.

(10) Patent No.: US PP29,754 P2
(45) Date of Patent: Oct. 16, 2018

(54) *PETUNIA* PLANT NAMED 'KLEPH16333'

(50) Latin Name: *Petunia hybrida*
Varietal Denomination: KLEPH16333

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/731,046

(22) Filed: Apr. 10, 2017

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.1, 13, 356.13, 1
CPC ..... A01H 5/02; A01H 5/00; A01H 6/824
See application file for complete search history.

(56) References Cited

U.S. PATENT DOCUMENTS

PP25,595 P2 * 5/2015 Dummen ..... A01H 5/02
Plt./356.13

OTHER PUBLICATIONS

Dummen Orange. *Petunias* Red Fox Peppy, retrieved on Apr. 4, 2018, retrieved from the Internet at https://www.dummenorange.com/flippingbooks/catalog-spring2016-DE-GB-NL/files/assets/common/downloads/page0159.pdf, p. 159. (Year: 2018).*

Royal Horticultural Society *Petunia* Peppy Neon ='Duepepneo', retrieved on Apr. 4, 2018, retrieved from the Internet at https://www.rhs.org.uk/Plants/348128/i-Petunia-i-Font-Face-times-New-Roman-Peppy-Neon-FONT-Duepepneo-sup-(PBR)-sup/Details, one page. (Year: 2018).*

* cited by examiner

*Primary Examiner* — June Hwu
(74) *Attorney, Agent, or Firm* — Barbara Campbell; Cochran Freund & Young LLC

(57) ABSTRACT

A new *Petunia* plant particularly distinguished by yellow flowers with red-purple stripes and a trailing habit, is disclosed.

1 Drawing Sheet

Genus and species: *Petunia hybrida.*
Variety denomination: 'KLEPH16333'.

BACKGROUND OF THE NEW PLANT

The present invention comprises a new and distinct variety of *Petunia*, botanically known as *Petunia hybrida*, and hereinafter referred to by the variety name 'KLEPH16333'. 'KLEPH16333' originated from a cross-pollination conducted in July 2013 in Latina, Italy between the proprietary female *Petunia* variety 'PH-2012-3379' (unpatented) and the proprietary male *Petunia* variety 'PH-2012-3533' (unpatented).

The seeds from the cross were sown and plants were grown in a greenhouse for evaluation, where an individual plant designated 'KLEPH16333' was selected from the group of plants in April 2014 in Latina, Italy. In May 2014, 'KLEPH16333' was first vegetatively propagated by terminal tip cuttings in Latina, Italy. 'KLEPH16333' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Yellow flowers with red-purple stripes; and
2. A trailing habit.

DESCRIPTION OF THE PHOTOGRAPH

This new *Petunia* plant is illustrated by the accompanying photograph of a plant grown in a plastic greenhouse in Stuttgart, Germany. The photograph was taken in June 2016 and shows the foliage and flowers of a 9-week-old plant grown in a pot.

The colors shown are as true as can be reasonably obtained by conventional photographic procedures.

DESCRIPTION OF THE NEW VARIETY

The following detailed descriptions set forth the distinctive characteristics of 'KLEPH16333'. The data which define these characteristics were collected from asexual reproductions carried out in Latina, Italy. Data was collected on plants grown 13-weeks from cultivation from potting in a plastic greenhouse in Latina, Italy in March 2017. Color references are to The R.H.S. Colour Chart of The Royal Horticultural Society of London (R.H.S.), 5$^{th}$ edition (2007).

Classification:
*Family.*—Solanaceae.
*Botanical.*—*Petunia hybrida.*
*Common.*—*Petunia.*
*Designation.*—'KLEPH16333'.

Parentage:

*Female parent*.—The proprietary female *Petunia* variety 'PH-2012-3379' (unpatented).

*Male parent*.—The proprietary male *Petunia* variety 'PH-2012-3533' (unpatented).

Plant:

*Vigor*.—Medium vigor.

*Habit*.—Trailing.

*Height* (*from top of soil*).—About 5.5 cm.

*Width* (*horizontal plant diameter*).—23.0 cm.

*Propagation*.—Terminal tip cuttings and tissue culture.

*Time to produce a finished flowering plant*.—About 13 weeks in the winter under short day conditions, and 7 weeks in the spring.

*Time to initiate and develop roots*.—2 to 3 weeks.

*Root description*.—Moderate density, moderate branching, white roots.

Stems:

*Average number* (*basal*).—12.

*Length of basal branches* (*from the base of the stem to the tip*).—12.0 cm.

*Internode length*.—1.0 cm to 1.8 cm.

*Diameter of branches* (*from midpoint*).—0.35 cm.

*Stem color*.—Varies between RHS 144A and RHS 144B.

*Anthocyanin*.—Absent.

*Texture*.—Tomentose.

Leaves:

*Arrangement*.—Alternate.

*Length*.—6.0 cm.

*Width*.—2.5 cm.

*Shape*.—From elliptic to spatulate.

*Apex*.—Broad acute.

*Base*.—Attenuate.

*Margin*.—Entire.

*Immature leaf color*.—Upper surface: RHS N137B. Lower surface: RHS N138A.

*Mature leaf color*.—Upper surface: RHS N137A. Lower surface: RHS N138A.

*Texture* (*both upper and lower surfaces*).—Tomentose.

*Venation pattern*.—Arcuate.

*Venation color*.—Upper surface: RHS 146B. Lower surface: RHS 145A.

*Petioles*.—Length: 1.5 cm. Diameter: 0.4 cm. Color: Varies between RHS 144A and RHS 144B. Texture: Tomentose.

Flower buds:

*Shape*.—Irregular oblong.

*Length*.—About 3.8 cm.

*Diameter*.—0.8 cm.

*Color at tight bud*.—RHS N144A at the margins, RHS N77A at the base and the veins.

*Texture*.—Slightly tomentose.

Inflorescence:

*Blooming habit* (*flowering season*).—Permanent flowering during spring and summer time.

*Inflorescence type*.—Sympodial, with monochasial growth.

*Number of flowers per node*.—1.

*Lastingness of individual blooms on the plant*.—7 to 10 days.

*Fragrance*.—Not detected.

*Flowers*.—Arrangement: Composed of 5 petals fused at the base. Diameter (flower face): 5.5 cm to 6.0 cm. Depth (total length of flower): 4.5 cm. Throat/Funnel: Length: About 3.0 cm. Diameter (at opening): 1.2 cm. Texture: Inner surface: Smooth. Outer surface: Pubescent. Color: Inner surface: RHS 200A (Brown) in the inner eye of the throat and in stripes at the upper part of the fused tube, along the fusion line, alternated with RHS 151A (Yellow-green) and RHS 151B (Yellow-green); strong conspicuousness of veins so as to be fused in a dark eye. Outer surface: Depending on the flowers, the most similar color is RHS N79A (Purple), sometimes alternated to RHS 1C (Green-yellow) toward the upper part of the throat, around the central vein of the petal. Petals: Color of petals, immature flower: Upper surface: Same color range as the mature flowers but the purple-red stripes along the fusion line are stronger than the mature flowers; very weak conspicuousness of veins, one visible central vein (RHS N144A on both surfaces). Color of petals, mature flower (fully opened): Upper surface: Along the fusion line of the petals, starting from the dark eye, RHS N79A (dark Purple) verging to RHS 71A (Red-purple) and RHS 71B (Red-purple) and RHS 153D (Yellow-green) around the central vein of the petal; the degree and distribution of the colors is playing on the plant and during the season; very weak conspicuousness of veins, one visible central vein (RHS N144A on both surfaces). Lower surface: RHS N77A (Purple) along the fusion line of the petals and verging to RHS 1C (Green-yellow) around the central vein of the petal color. Apex: Emarginate. Base: Fused. Shape: Funnelform. Margin: Entire. Strength of waviness: Weak. Degree of lobation: Weak. Calyx arrangement: Actinomorphic, composed of 5 sepals. Sepals: Color: Upper surface: Varies between RHS 137B and RHS 137C. Lower surface: RHS 137D. Length: About 1.8 cm. Width: 0.7 cm. Shape: Oblong. Apex: Broadly acute. Base: Fused. Margin: Entire. Texture (both upper and lower surfaces): Pubescent.

*Pedicels*.—Color: RHS 144A. Length: 3.5 cm. Diameter: 0.2 cm. Texture: Pubescent.

Reproductive organs:

*Stamens*.—Quantity: 5. Shape: Needle with elliptic head. Filament: Length: 0.8 cm to 1.0 cm. Diameter: 0.02 cm. Color: Varies between RHS N79A and RHS N79B. Anther: Shape: Oblong. Color: RHS 148D. Length: 0.3 cm. Diameter: 0.2 cm. Pollen: Color: RHS 188A. Amount: Abundant.

*Pistils*.—Quantity per flower: 1. Length: 2.0 cm. Stigma color: RHS 148B. Style color: RHS 144D at the base and RHS N79A at the top.

Fruit and seed set: No fruit and seed set observed to date.

Disease and pest/insect resistance: No disease and pest/insect resistance observed.

COMPARISON WITH PARENTAL LINES AND KNOWN VARIETY

'KLEPH16333' is a distinct variety of *Petunia* and is distinguished from its parents as described in Table 1.

TABLE 1

| Comparison with Parental Lines | | | |
|---|---|---|---|
| Characteristic | 'KLEPH16333' | Female Parent 'PH-2012-3379' | Male Parent 'PH-2012-3533' |
| Flower color | Yellow with red-purple stripes | White with pink zones | Yellow with dark-burgundy stripes or unregular zones |

'KLEPH16333' is a distinct variety of *Petunia* and differences between 'KLEPH16333' and the commercial variety 'Duepepneo' (U.S. Plant Pat. No. 25,595) are described in Table 2.

TABLE 2

| Comparison with Similar Variety | | |
|---|---|---|
| Characteristic | 'KLEPH16333' | 'Duepepneo' |
| Flower color | Yellow with red-purple stripes | White yellow flowers with red-purple stripes along the fused parts of the corolla lobe |

We claim:

1. A new and distinct variety of *Petunia* plant named 'KLEPH16333' as illustrated and described herein.

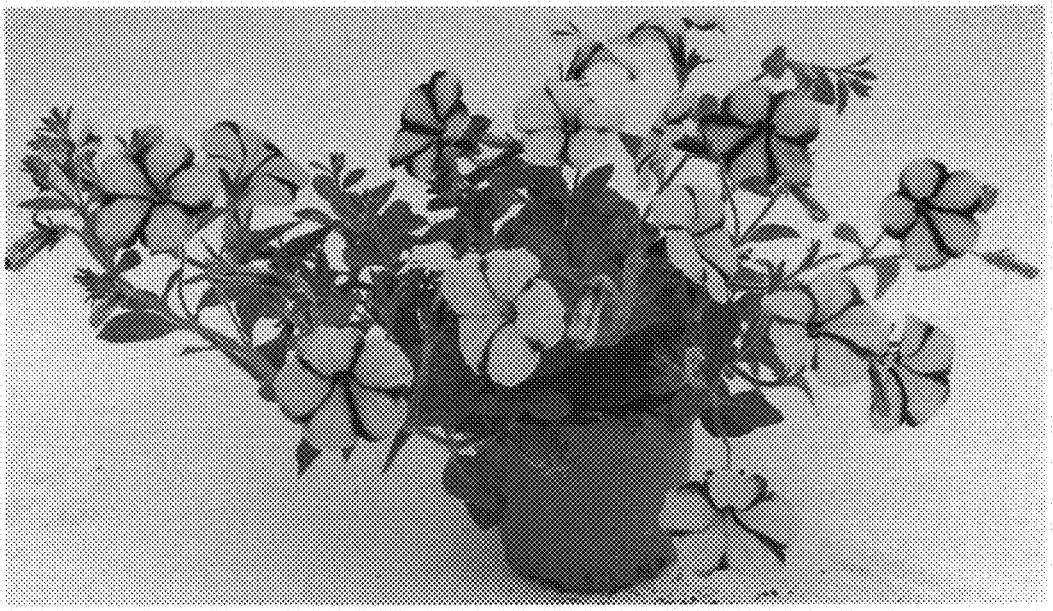

* * * * *